United States Patent [19]
Smith et al.

[11] Patent Number: 5,644,834
[45] Date of Patent: *Jul. 8, 1997

[54] PROCESS FOR MANUFACTURING TAPER POINT SURGICAL NEEDLES

[75] Inventors: Daniel Smith, Manalapan Township; Bernard M. Willis, East Brunswick; Kenneth P. Marschke, Jr., Medford; Barry Littlewood, Harmony; Vulgens Schoen, Stockton; Carl Gucker, Branchburg; Michael Nordmeyer, Neshanic Station, all of N.J.; Thaddeus Miklewicz, Nazareth, Pa.

[73] Assignee: Ethicon, Inc., Somerville, N.J.

[*] Notice: The term of this patent shall not extend beyond the expiration date of Pat. No. 5,477,604.

[21] Appl. No.: 621,375

[22] Filed: Mar. 25, 1996

Related U.S. Application Data

[63] Continuation of Ser. No. 429,446, Apr. 27, 1995, abandoned, which is a continuation of Ser. No. 146,681, Nov. 1, 1993, Pat. No. 5,477,604.

[51] Int. Cl.$^6$ ....................................... B23P 13/04
[52] U.S. Cl. ................ 29/557; 29/563; 29/33 F; 451/140; 451/184; 451/244
[58] Field of Search ................ 606/222, 223; 163/1, 4, 5, 6; 29/7, 33 F, 56.5, 423, 558, 559, 557, 563, 564, 564.3, 564.6, 564.7; 451/48, 49, 54, 130, 140, 182, 184, 242, 244; 83/35, 40; 470/34–40

[56] References Cited

U.S. PATENT DOCUMENTS

| | | | |
|---|---|---|---|
| 963,987 | 7/1910 | Bohin | 163/5 |
| 2,110,931 | 3/1938 | Dyer et al. | 451/184 |
| 3,627,866 | 12/1971 | Laws | 83/35 |
| 4,384,942 | 5/1983 | Glowacki | 451/184 |
| 4,631,897 | 12/1986 | Slavicek | 53/399 |
| 5,388,374 | 2/1995 | Samsel | 451/245 |
| 5,518,438 | 5/1996 | Munoz et al. | 451/245 |

FOREIGN PATENT DOCUMENTS

| | | | |
|---|---|---|---|
| 2121943 | 11/1972 | Germany . | |
| 2637788 | 2/1978 | Germany | 451/382 |
| 2043502 | 10/1980 | United Kingdom . | |

*Primary Examiner*—David P. Bryant
*Attorney, Agent, or Firm*—Emil Richard Skula

[57] ABSTRACT

A process for manufacturing wire or needles having a taper point. Needle or wire blanks are cut from a roll of wire and mounted to a carrier strip. The carrier strip and needles are moved through a succession of forming and trimming and grinding stations. The blanks are preferably rotated in the strip while being ground.

1 Claim, 15 Drawing Sheets

PROCESS FOR MANUFACTURING TAPER POINT SURGICAL NEEDLES

This is a continuation of application Ser. No. 08/429,446, filed Apr. 27, 1995, now abandoned, which is a continuation of application 08/146,681, filed Nov. 1, 1993, now U.S. Pat. No. 5,477,604.

TECHNICAL FIELD

The field to which this invention pertains is surgical needles, more specifically, a method of manufacturing taper point surgical needles.

BACKGROUND OF THE INVENTION

Surgical needles and methods of manufacturing surgical needles are well known in the art. Surgical needles typically consist of a shaft-like member, which may be curved or straight. The member has a distal piercing point and a proximal end for mounting or receiving a suture. Surgical needles are typically classified as either taper-point needles, wherein the diameter of the shaft tapers to a piercing point, or cutting edge needles wherein the needles have various cutting edges along with piercing points to assist in penetrating various types of tissue.

Surgical sutures may be attached or mounted to the proximal ends of surgical needles in various ways. One common way is to have a channel formed into the proximal end of the needle. The channel end typically is die-formed into a needle during the manufacturing process and consists of a cavity. When a surgical suture end or tip is placed into the cavity, the channel end is hit with a die one or more times under pressure forcing the sidewalls closed tightly about the suture tip to prevent the suture from separating from the needle. The process of mounting a suture tip to the proximal end of a needle is known in the art as swaging. Another manner in which a suture may be mounted to a surgical needle is by drilling a hole, commonly referred to in the art as blind hole, into the proximal end of the needle. This can be done using conventional mechanical drilling apparatuses or conventional laser drilling apparatuses. The end or tip of a suture is then inserted into the drilled hole and the section of the proximal end of the needle surrounding the blind hole is swaged in a conventional manner by compressing with various conventional dies. It is also known to mount sutures to surgical needles using conventional adhesives.

Surgical needles are conventionally manufactured from surgical grade alloys, such as surgical grade stainless steel, which are purchased from manufacturers in the form of rod or wire. The rod is drawn into wire and rolled onto a spool. The initial step in the manufacture of surgical needles is to remove the wire from the spool, degrease or clean if required, and then cut the wire into sections known as needle blanks. Each blank will have a length greater than the length of the finished needle, since material will necessarily be removed from the blank during the needle manufacturing process.

A conventional process for manufacturing a taper point needle typically consists of cutting wire into needle blanks and taking each needle blank and subjecting the blank to a series of grinding operations. This is conventionally done in the following manner. The needle blanks are fed into a conventional belt\stone grinding machine where they are given a distal tip. The needles are then transported individually or in bulk to a conventional needle drilling station wherein the needles are drilled using conventional carbide or tool steel drill bits to provide a proximal suture mounting cavity. The needles are then typically degreased and moved in bulk to a conventional belt/stone grinding machine for the finish taper grind and then to a curving machine to produce a conventional curved configuration. The needles are then cleaned, heat treated and may be electrochemically treated to additionally finish the needles. The conventional process is a batch process requiring the handling of the needles in bulk containers to transport them to and from the various work stations. Needles may become damaged or intermingled during such bulk transfers. In addition, the needles must typically be individually mounted in chucks in each machine at each work station. Although this chuck mounting step may in some circumstances be automated, it is typically a time consuming, labor intensive operation.

One conventional method of manufacturing cutting edge needles consists of initially cutting wire into blanks as described above. The distal tips of the needle blanks are then rotary swaged in a rotary swaging machine to produce a conical point having a spud. The spud is next partially cut and the needle blanks are then moved to a belt/stone grinder and mounted into chucks wherein the distal tip of each needle blank is given the final grind to create the necessary shape for bayonet closed die forming. The needle blanks are then moved in bulk or by chuck to a die station where each needle blank is die-formed. The needle blanks are then subjected to a series of grinding operations in a conventional belt/stone grinding machine to produce the cutting edge shape, for example, eight or more separate grinds. The needle blanks must be removed from the chucks and remounted in chucks after and prior to each grinding step, typically by using a walking beam mechanism. The extensive bulk and manual handling required by this process may result in damage to the needles, including the dulling of the points. In addition, the needle machines used in the prior art processes are operator dependent. Each operator tends to set up a machine differently resulting in variability in needle geometry and performance characteristics. Since surgical needles are quality control tested prior to release, the problems associated with the prior art processes tend to result in a financial burden upon the manufacturer in that a significant amount of the needles produced may have to be rejected and destroyed.

The previously described processes are labor intensive and typically utilize low speed, low output equipment. The needles are typically manually handled and transferred in bulk containers between various work stations or machines. In addition, numerous grinding steps are usually required. Often, needles are damaged, including the dulling of needle points, due to the extensive handling and numerous grinding steps which are present in these processes. It is known that grinding operations are by their very nature imprecise resulting in wide variations in the dimensions of the finished needles. This imprecision resultingly yields a significant degree of geometric variability.

Accordingly, what is needed in this art is a process for manufacturing taper point needles which is efficient and substantially minimizes manual handling and also minimizes grinding.

DISCLOSURE OF THE INVENTION

Therefore, it is an object of the present invention to provide a novel process for manufacturing taper point needles.

It is a further object of the present invention to provide a process for improving the manufacture of taper point surgical needles by minimizing the number of grinding operations which must be used.

It is a further object of the present invention to provide a taper point needle manufacturing process which can be automated as a substantially continuous process, eliminating or minimizing the need for batch processing.

Accordingly, a process for manufacturing taper point surgical needles by progressively working a needle blank is disclosed. The process of the present invention consists of the initial step of cutting needle blanks from a roll of wire and mounting the blanks in a carrier. The carrier transports the blanks to a succession of work stations. At an initial trim station, the distal end of the needle blank is cut at an angle with respect to the longitudinal axis of the needle blank on at least one plane and two preferably opposed planes. Next the needle blank is transported to an optional work station where it is rotated, for example 90° from its previous position in the carrier. Then it is moved to at least one additional trim station where similar angulated cuts are made to the distal end of the needle blank on the remaining uncut sections. Then each needle blank is moved to a grinding station wherein the needle blank is rotated about its longitudinal axis in the carrier as the distal tip of the needle blank is ground with a high speed grinding wheel parallel to the longitudinal axis of the needle blank. The needle is then cleaned, heat treated and electrochemically treated. The finished needle is optionally siliconized.

Yet another aspect of the present invention is a method of manufacturing a taper point surgical needle by progressively forming a needle blank. The process consists of the initial step of cutting needle blanks from a roll of wire and mounting the blanks in a carrier. The carrier transports the blanks to a succession of work stations. At the initial work station, the needle blank is coined in at least one conventional closed die having a cavity. Each needle blank is then moved successively to a trim station where flash is trimmed from the needle blanks using a punch and die. Optionally, the needle blank can be transported to one or more additional coining and trimming stations. Then each needle blank is moved to a grinding station wherein the needle blank is rotated about its longitudinal axis in the carrier as the distal tip of the needle blank is ground with a high speed grinding wheel parallel to the longitudinal axis of the needle blank. The needle blank is then cleaned, heat treated, and electrochemically treated. The finished needle is optionally siliconized.

Yet another aspect of the present invention is a method of manufacturing a wire member having a distal taper point by progressively forming a wire blank. The process consists of the initial step of cutting wire blanks from a roll of wire and mounting the blanks in a carrier. The carrier transports the blanks to a succession of work stations. At the initial work station, the wire blank is coined in at least one conventional closed die having a cavity. Each blank is then moved successively to a trim station where flash is trimmed from the needle blanks using a punch and die. Optionally, the blank can be transported to one or more additional coining and trimming stations. Then each wire blank is moved to a grinding station wherein the wire blank is rotated about its longitudinal axis in the carrier as the distal tip of the wire blank is ground with a high speed grinding wheel transverse to the longitudinal axis of the blank. The wire blank is then optionally cleaned, heat treated and electrochemically treated. The finished wire member is optionally siliconized.

Still yet another aspect of the present invention is a method of manufacturing a wire member having a distal taper point by progressively working a wire blank. The process consists of the initial step of cutting wire blanks from a roll of wire and mounting the blanks in a carrier. The carrier transports the blanks to a succession of work stations. At the initial trim station, the distal end of the wire blank is cut at an angle with respect to the longitudinal axis of the wire blank on at least one plane and preferably two planes. Next the wire blank is transported to a station where it is rotated, for example 90° from its previous position in the carrier. Then it is moved to at least one additional trim station where similar angulated cuts are made to the distal end of the wire blank on the remaining uncut sections. Optionally, the needle blanks are moved to a top and bottom flattening station wherein top and bottom flat sides are formed. Then each wire blank is moved to a grinding station wherein the wire blank is rotated about its longitudinal axis in the carrier as the distal tip of the wire blank is ground with a high speed grinding wheel parallel to the longitudinal axis of the needle blank. The wire blank is then optionally cleaned, annealed and electrochemically treated. The finished wire member is optionally siliconized.

Yet another aspect of the present invention is a method of manufacturing a surgical needle or a wire member having a taper point. The method comprises mounting a needle blank or wire blank in a carrier and moving each needle or blank to at least one trim station and trimming the blank in at least one plane. Then, the blank is move to a grinding station where the blank is optionally rotated in the carrier while the needle is ground parallel to the longitudinal axis of the blank.

Yet a further aspect of the present invention is a method of manufacturing a surgical needle or a wire member having a taper point. The method comprises mounting a needle blank or wire blank in a carrier and moving each needle or blank to at least one coin station and coining the blank. Then, the blank is move to a grinding station where the blank is optionally rotated in the carrier while the needle is ground parallel to the longitudinal axis of the blank.

Still a further aspect of the present invention is a method of manufacturing a taper point needle or a wire member having a taper point wherein a plurality of needle or wire blanks is mounted to a carrier. The carrier is moved to a grinding station wherein the grinding means is orbitally rotated about each blank to form a taper point.

Still yet a further aspect of the present invention is a method of manufacturing a taper point needle or a wire member having a taper point wherein a plurality of needle or wire blanks is mounted to a carrier. The carrier is moved to a trim station wherein the blank is trimmed or sheared in multiple planes to form a taper point.

Other features and advantages of the invention will become more apparent from the following description and accompanying drawings.

BEST MODE FOR CARRYING OUT THE INVENTION

Figure 1:
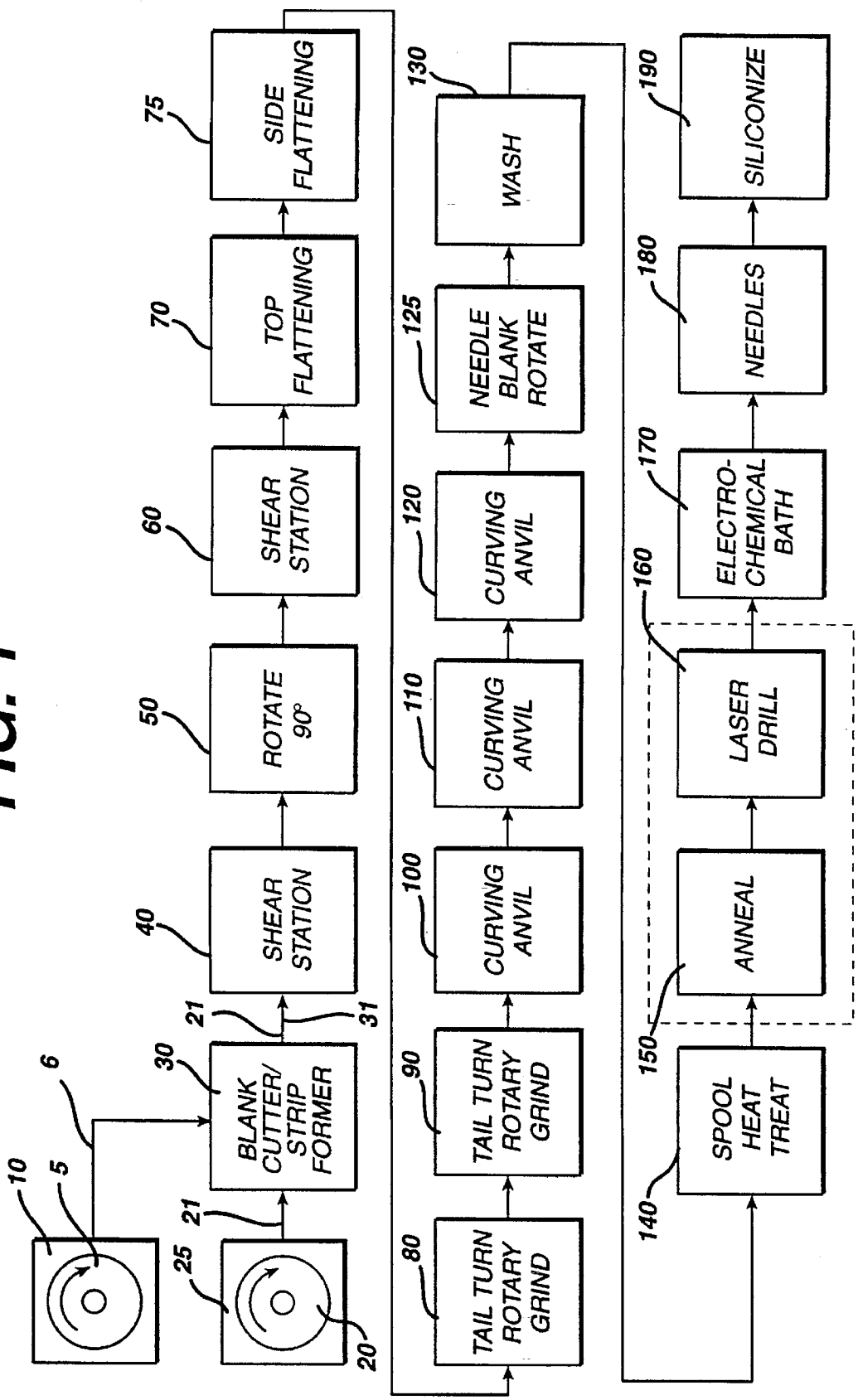
FIG. 1 is a flow diagram illustrating a process of the present invention wherein the distal end of the needle blank is trimmed prior to grinding.

Referring to FIG. 1, a flow diagram for a needle manufacturing process of the present invention is illustrated.

Figure 3:
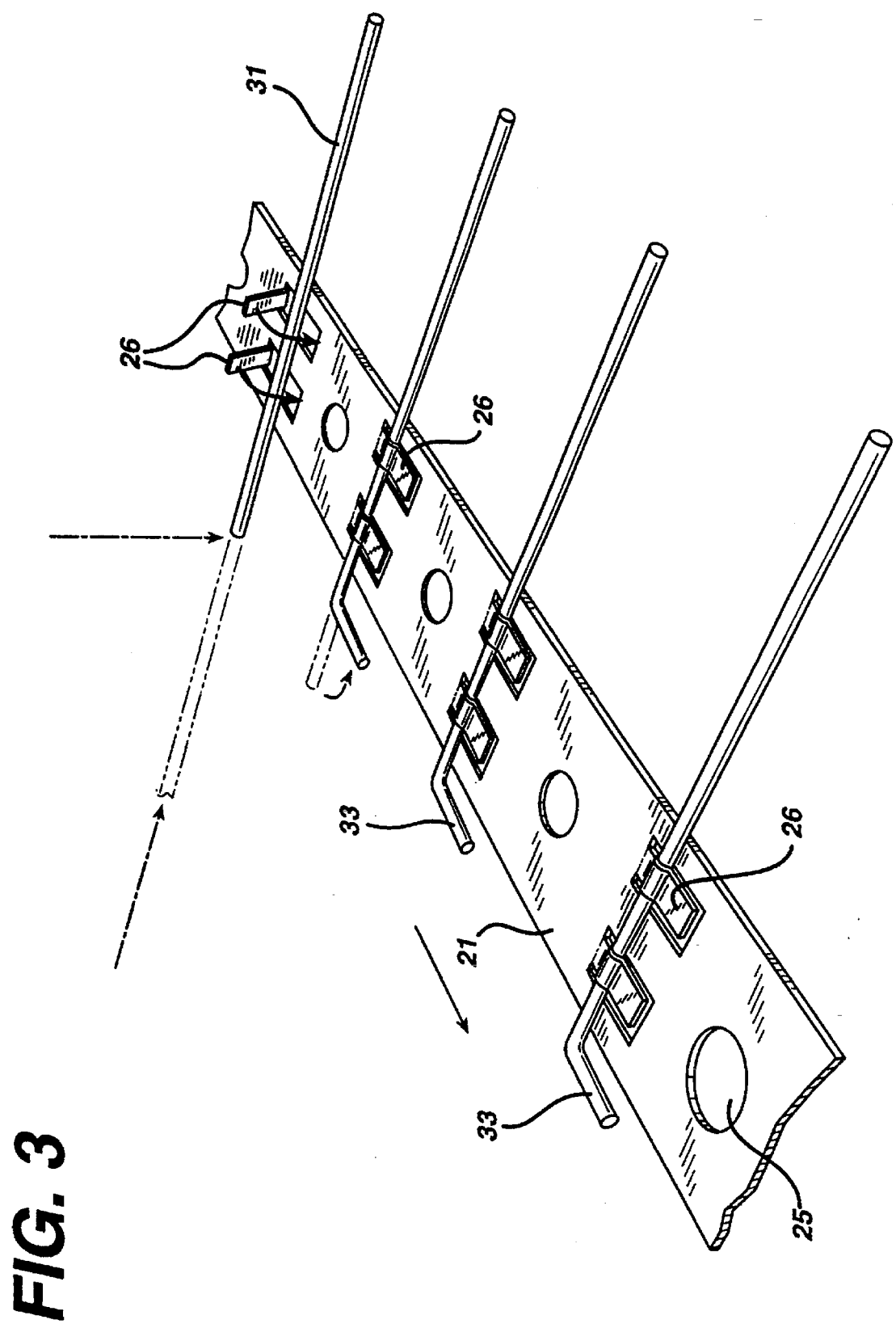
FIG. 3 is a perspective view of a needle blank after it has been cut by the blank cutter/strip former machine; the needle blank is seen mounted in a section of carrier strip with the proximal end or tail bent.
Figure 4:
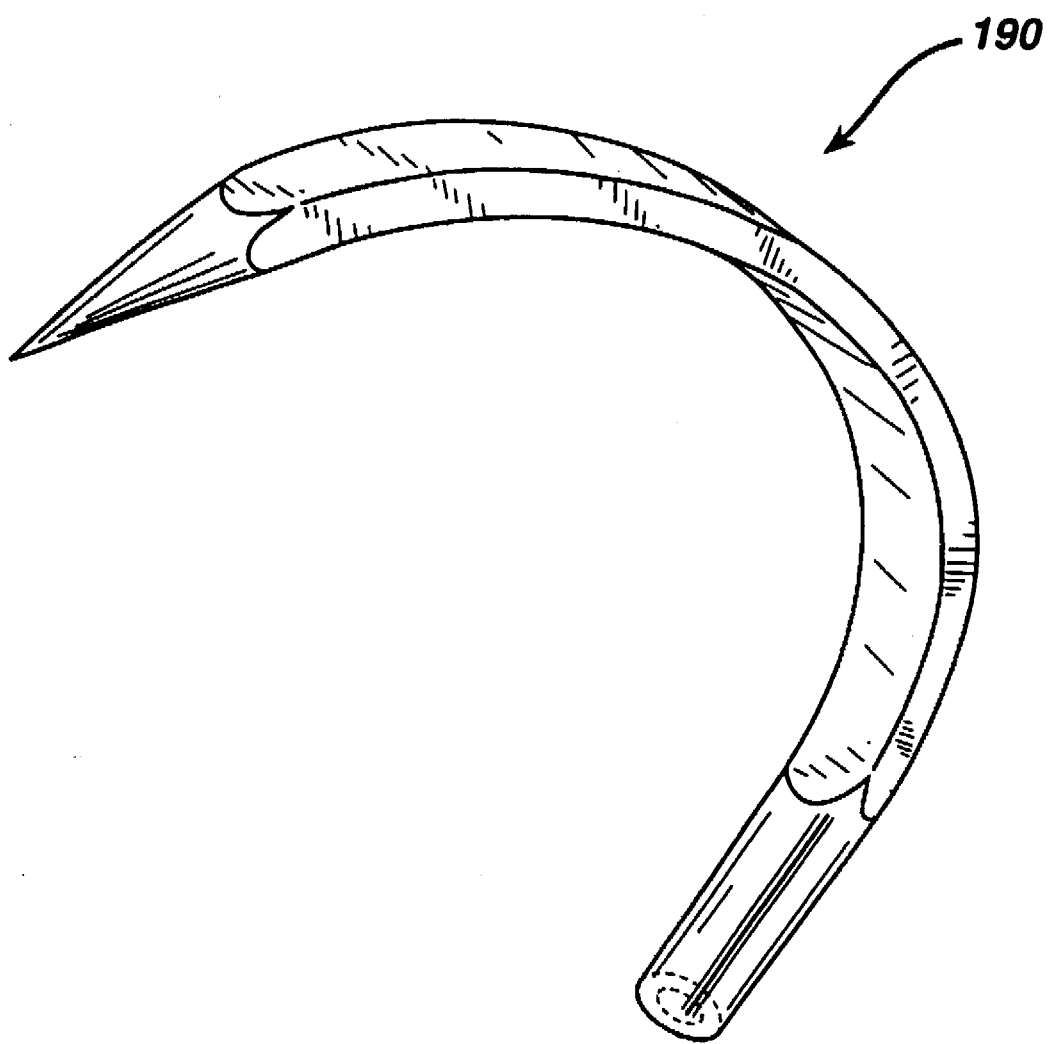
FIG. 4 is a perspective view of a taper point needle produced by the process of the present invention.

Initially wire 6 from roll 5 is fed by a conventional gripper/feeder machine 10 to blank cutter/carriage strip former machine 30. The roll 5 is rotatably mounted in gripper feeder/10. Simultaneously, the carrier strip 21 is fed from carrier strip roll 20, which is rotatably mounted in conventional gripper/feeder machine 25 to blank cutter/carriage strip former machine 30. In blank cutter/carrier strip former machine 30, the wire 6 which is fed from gripper/feeder 10 is cut into lengths which are conventionally referred to as needle blanks 31. As the needle blanks 31 are being cut, the blank cutter/carrier strip former 30 is simultaneously processing the carrier strip 21. The carrier strip 21 typically consists of a steel strip known as a bandoleer. The strip will be sufficiently thick, sufficiently wide and sufficiently flexible to effectively move and retain needle blanks while being capable of being die punched and formed. Preferably the bandoleer is made of a flexible metal such as cold rolled steel and equivalents thereof. However, the bandoleer may also be made from polymeric materials such as engineered, reinforced polymers and equivalents thereof. The wire 6 being fed from gripper/feeder 10 is cut into lengths which are conventionally referred to as needle blanks 31 within blank cutter/carriage strip former machine 30. As the needle blanks 31 are being cut, the blank cutter/carrier strip former 30 is simultaneously processing the carrier strip 21 in the following manner. Carrier strip 21 is processed to receive needle blanks 21 and to engage indexing controls within the various work stations. The carrier strip 21 is die cut, formed and crimped to produce a carrier strip having indexing pilot holes 25 and crimps which form mounting tabs 26 for receiving, engaging and holding needle blanks 31. A section of carrier strip 21 having needle blanks 31 mounted therein is seen in FIG. 3. Then, needle blanks 31 are cut and inserted into the mounting tabs 26 of carrier 21 by inserting the wire 6 into each tab 26 and then cutting the wire 6 to from a needle blank 31. The tabs 26 are then crimped to retain the needle blanks 31. The proximal ends 32 of the needle blanks 31 are bent approximately 90° from the longitudinal axis of the needle blank 31 to form tails 33. If desired, the carrier strip 21 may be a continuous endless carrier which is reused during the needle manufacturing process. The strip would have the pilot holes 25 and tabs 26 and needles would be removed from the endless carrier at a convenient stage of the process, and remounted to one or more additional carrier strips. One skilled in the art will appreciate that the needle blanks 31 may also be mounted to the carrier strip 21 by alternate methods, if desired although not preferred, including welding, clips, adhesives, snap fits, and the like. The bandoleer strip could, if desired be replaced by a member comprising a lattice of two or more wires. The blank cutter/carrier strip cutter machine 30 consists of several machines and operations as described below including a strip forming tool station 39, wherein the pilot holes 25 and tabs 26 are formed, strip preparation tool station 38 wherein the tabs 26 are opened, wire cut-off and strip crimping tool station 39 wherein wire is fed into tabs 26 and blanks 31 are cut and formed, and tail bending station 39A wherein the proximal tail of the needle blank 31 is bent to facilitate rotation in the carrier strip 21.

Next, the carrier strip 21 having needle blanks 31 mounted therein is moved by a conventional gripper feeder mechanism to first shear station 40. Movement of the carrier strip to the work stations is indexed to precisely align each needle blank 31 within any of the work stations in the following manner. The carrier strip 21 has indexing pilot holes 25 punched into the carrier strip 21 by the blank cutter/strip former 30. The pilot holes mate with pilots mounted at each work station which engage the pilot holes. The pilots consist of a moveable pin which extends into the pilot holes 25. The strip 21 is indexed by a strip feed wherein pilot pins enter, engage and lock the carrier strip 21 into a precisely aligned position within a work station tool. Needle blanks 31 may be mounted at different intervals along the carrier strip 21, for example, from 0.5" to 1.0" intervals. Because of the spatial layout of the tooling, not every needle blank 31 is within a work station at a given time. Some needles will be indexed into a particular work station while other needles will be queued up waiting to enter work stations.

Figure 2A:
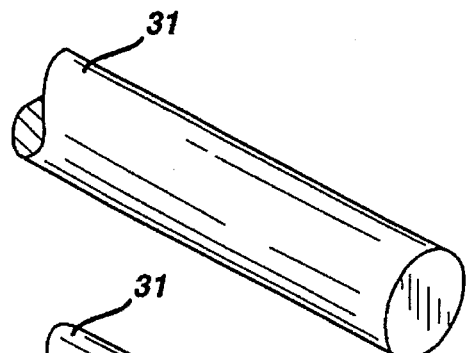
FIG. 2A–2F illustrate a progression of cross-sectional perspective views of the needle blank after having been processed through each step of the process.
Figure 2B:
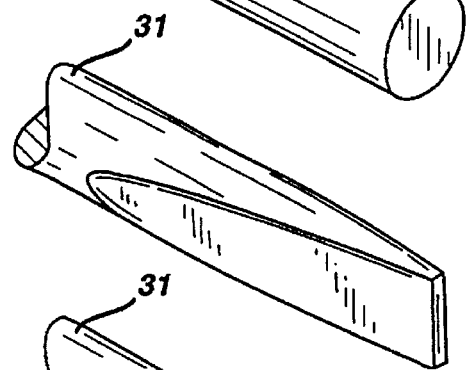
Figure 2C:
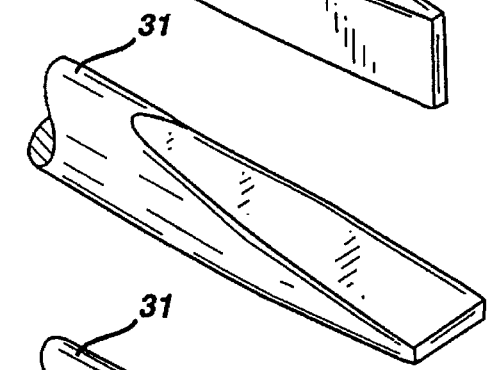
Figure 2D:
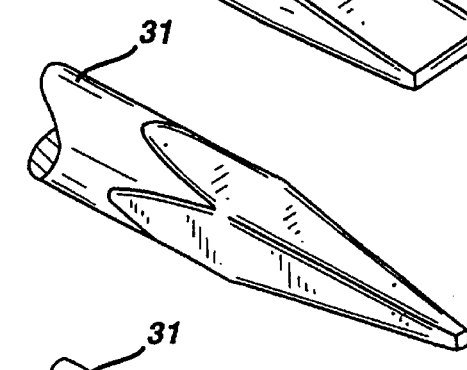
Figure 2E:
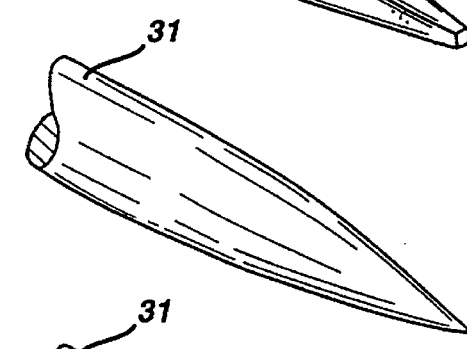
Figure 2F:
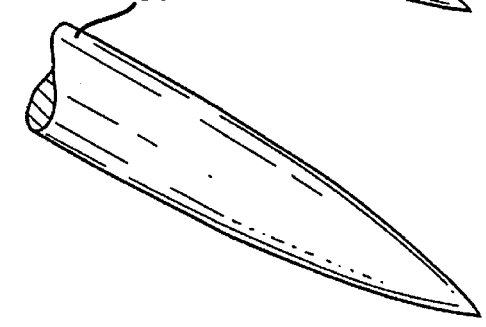
Figure 6:
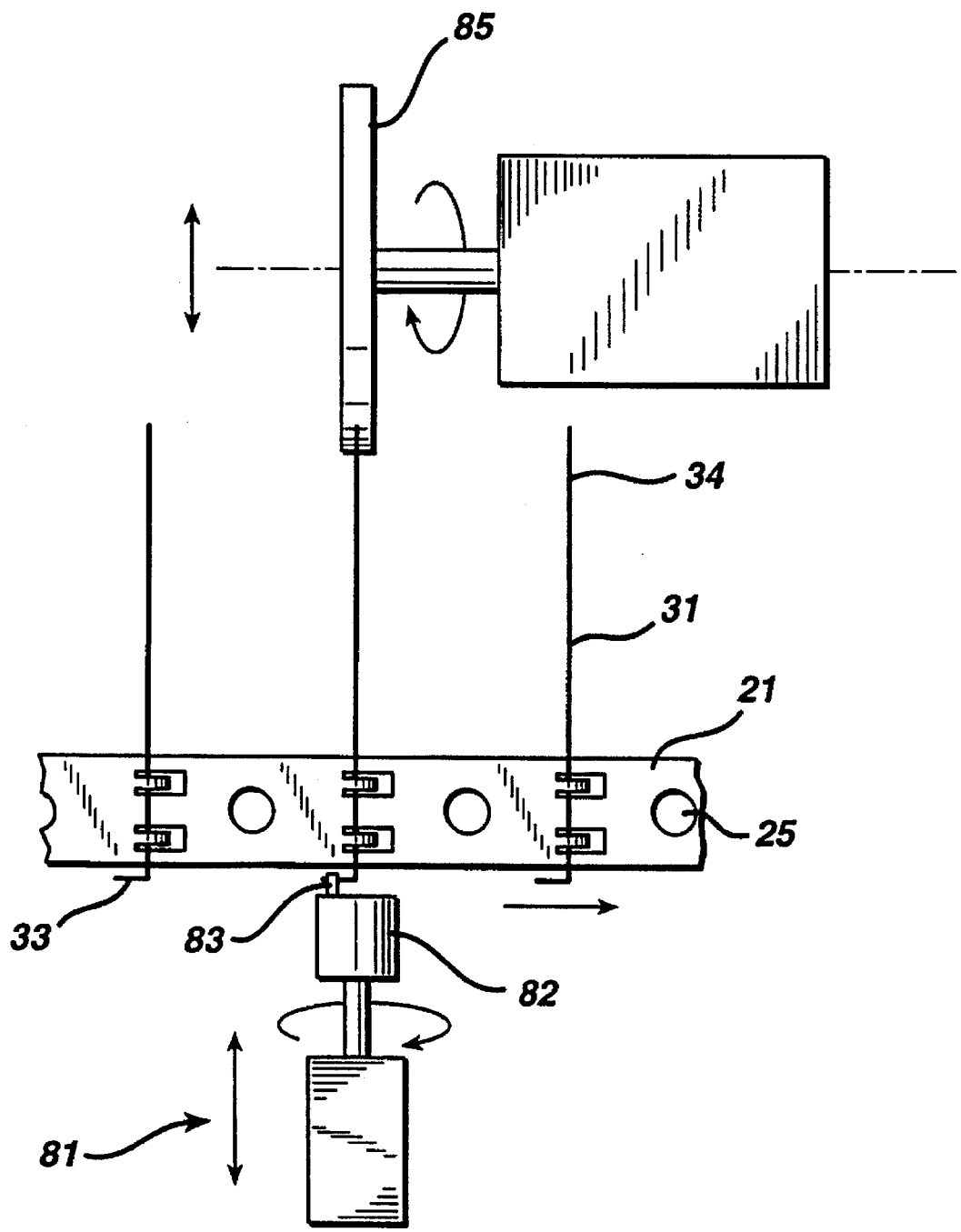
FIG. 6 is a schematic of a tail turn rotary grinding assembly; the needle blank is rotated clockwise in the carrier strip while the rotary wheel grinder grinds the needle in a direction parallel to the longitudinal axis of the needle blank.

Shear station 40 consists of a conventional die and punch. The needle blank 31 is trimmed or sheared in station 40 by having the distal end 34 of the needle blank 31 cut or sheared at an angle, preferably an acute angle, with respect to the longitudinal axis of needle blank 31 along at least one plane and preferably two opposite planes. The needle blank prior to entering shear station 40 will have a distal configuration as seen in FIG. 2A. The needle blank 31 exiting trim station 40 may have a configuration as seen in FIG. 2B. Next the needle blank 31 is moved to optional station 50 where it is rotated as required to trim the remainder of the needle blank, preferably 90° in the carrier 21 as seen in FIG. 2C. If desired multiple trim stations may be used to form a needle blanks 31 having more that four planes trimmed, for example, multiple trims may be used to form a needle blank having a distal cross-section which is n-polyhedral. Next carrier 21 and the needle blank 31 are moved to shear station 60 where the needle is trimmed along the remaining untrimmed opposed sides to produce a configuration as illustrated in FIG. 2D. If desired, the needle blank 31 can be trimmed only one time to form a single trim plane; or, it may be trimmed more than four times to form multiple planes. The needle blank 31 is then moved to the top and side flattening stations 70 and 75 where the needle blank 31 is appropriately formed by giving it flats. Then the needle blank 31 is moved to a tail turn rotary grind station 80. Referring to FIG. 6, tail turn rotary grind station 80 consists of a tail turning device 81 and preferably a pair of grinding wheels 85, although one grinding wheel may be used. In a preferred embodiment, the device 81 consists of pin 83 mounted to a rotating disc 82 which engages the tail 33 and rotates the needle blank 31 about its longitudinal axis within the carrier strip 21 (see FIGS. 3 and 6). The distal end of needle blank 31 is simultaneously ground to a tapered point by the grinding wheels 85. The needle blank 31 and the wheels 85 are preferably moved with respect to each other during the grinding. Each grinding wheel 85 has one half of the profile of the desired taper point needle configuration. However, if desired a single grinding wheel may be used or conventional grinding wheels not having a contour may be used. The grinding wheel 85 or wheels 85 may have an angular or other profile. For the sake of clarity, only one grinding wheel 85 is seen in FIG. 6. As the needle blank 31 is turned by the device 81, the grinding wheels 85 grind the distal end of the needle blank 31 parallel to the longitudinal axis of the needle blank 31. The needle blank 31 has a distal configuration as seen in FIG. 2E after exiting grinding station 80. The carrier strip 21 and needle blank 31 are next transported to tail turn rotary grind station 90 for processing similar or identical to that which occurs in tail turn rotary grind station 80 using similar or identical equipment. The needle blank 31 will have a distal configuration as seen in FIG. 2F after having been processed in tail turn rotary grind station 90. The tail turning and wheel grinding speeds will be sufficient to remove material effective to produce the desired taper point configuration. This will depend on material types and sizes as well as grinding media type and wheel configuration. The grinding media will typically be coarser in the first grinding station and finer in the second or additional grinding stations. Although not preferred, an alternate method of grinding useful in the process of the present invention is to maintain the needle blank 31 in a fixed configuration in the carrier such as by welding and to orbitally move grinding wheel 85 about the needle blank 31. It will also be appreciated that equivalent material removal devices can be used including a shearing device similar in operation to a pencil sharpener and the like.

The term "taper point" as used herein is defined to mean the distal end of a needle or needle blank (or wire member) having a taper profile which tapers from a maximum dimension to a distal minimum wherein the distal point may have a variety of radii ranging from a piercing point to the original diameter of the wire used to manufacture the needle or needle blank (or wire member).

The carrier strip 21 and each needle blank 31 are then moved to the optional multiple curving anvil stations 100, 110 and 120 where the needle blank 31 is given a conventional curved configuration of a surgical needle. Next, the needle blanks 31 are optionally rotated in needle blank rotation station 125 using conventional mechanical means to rotate the blank 31 in tabs 26 of carrier 21 to facilitate, e.g., rolling onto a spool. Then, the needle blanks 31 and the carrier strip 21 are optionally washed in wash station 130. The needle blanks 31 and carrier 21 are then rolled onto a conventional spool in a conventional manner using a conventional spooling apparatus. If desired the carrier strip 21 containing needle blanks 31 may be cut into strips for further processing. Next, the spool or tray containing needle blanks 31 and the carrier strip 21 is moved to optional spool heat treat station 140 where the needle blanks 31 are heated with or without a controlled gas environment in an oven at a sufficient temperature for a sufficient amount of time to effectively improve the mechanical strength of the needle blanks 31.

Next, the spool or tray containing the carrier strips 21 and the needle blanks 31 are moved to an optional annealing apparatus 150 where the proximal ends of the needle blanks 31 are annealed. The needles are heated in a conventional annealing process at a sufficient temperature and held for a sufficient length of time at that temperature to effectively anneal the proximal ends of the needle blanks 31. One reason annealing may be used is to improve swaging. Annealing apparatus 150 consists of any conventional apparatus including a flame, conventional oven, resistance heating, induction heating, etc.

Next, the carrier strips 21 containing needle blanks 31 are moved to laser drilling station 160. Optionally, the needles are removed from carrier strip 21 and remounted to a second carrier strip. Preferably the needle blanks remain on the carrier strip 21 and the strip 21 with the needle blanks 31 is fed to the laser drilling apparatus. The needle blanks 31 mounted to the second carrier strip are fed to a laser drilling apparatus wherein a suture mounting hole is drilled into the proximal end of each needle blank. The hole which is drilled by the laser is commonly referred to as a blind hole. The suture mounting hole if desired may also be mechanically drilled or drilled through other conventional methods including electron discharge techniques, etc. The loose needle blanks 31 can then be additionally cleaned and the needle blanks may be mounted into an additional carrier. Then, the needle blanks 31 are optionally washed and may, if desired, be placed into an optional electrochemical bath 170. The needle blanks 31 are maintained in the bath 170 for a sufficient time to effectively finish the needle blank 31. The finished needles 180 are then removed from the electrochemical bath 170, and washed if necessary. If desired, the needles 180 may be siliconized at siliconizing station 190 by treating the needles 180 with conventional siliconizing materials in a conventional manner using conventional equipment, e,g., immersion in a tank of siliconizing material.

If desired, the above-described process may be modified by having a single trim step prior to grinding the needle blank. In addition, the process may also be modified by not rotating the needle in the carrier while grinding. In such a case, the grinding would be accomplished with the grinder orbitally rotated about the needle blank. In yet another variation of the above described process, the needle is not ground, the point is formed by shearing or trimming in at least four planes to form a blank having a distal cross-section which is n-polyhedral.

Figure 7:
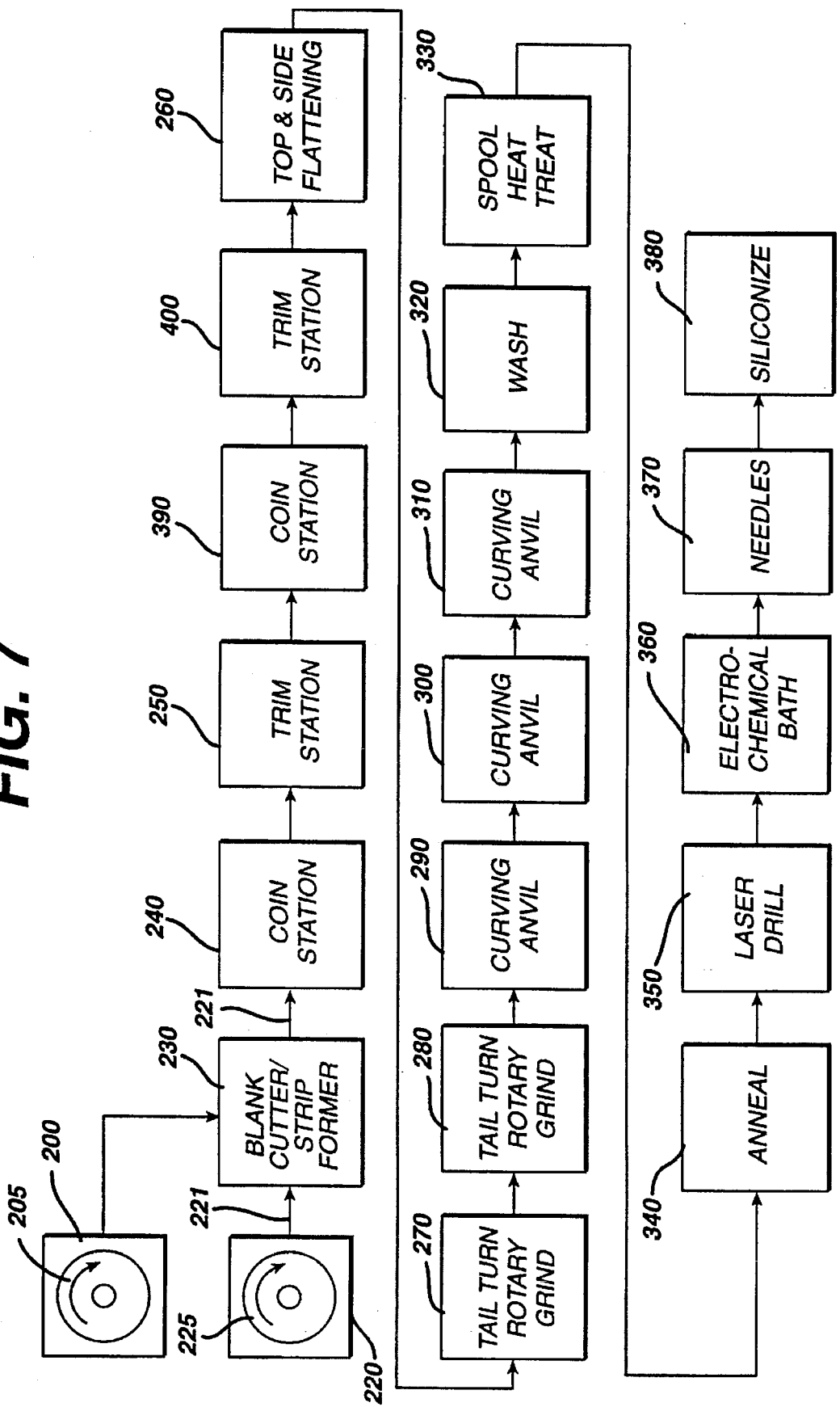
FIG. 7 is a flow diagram illustrating an alternate process for forming taper point needles wherein the needle blanks are coined and trimmed prior to the grinding step.
Figure 9:
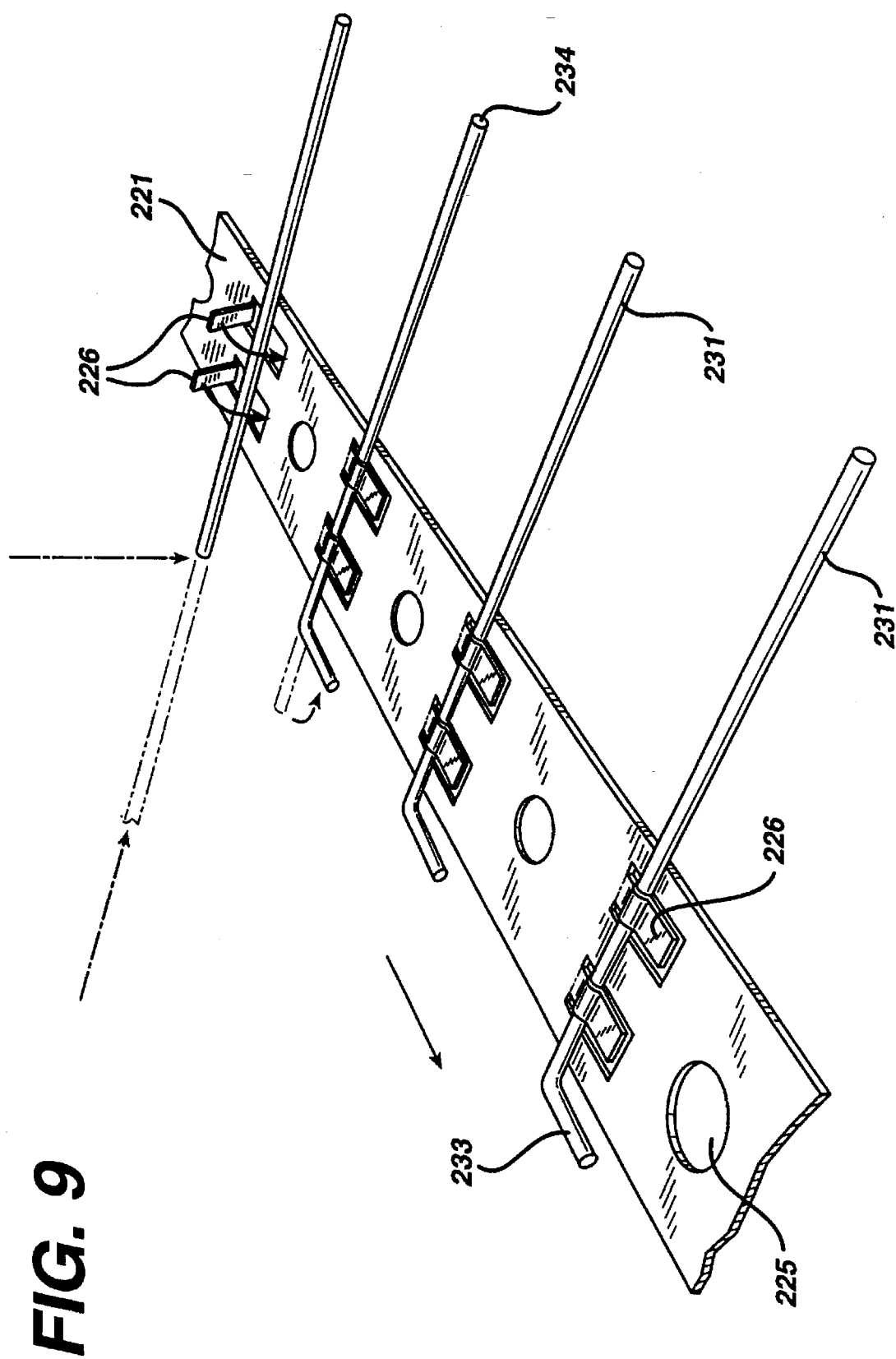
FIG. 9 is a perspective view of a needle blank after it has been cut by the blank cutter/strip former machine; the needle blank is shown mounted in a section of carrier strip with the proximal end or tail bent.
Figure 10:
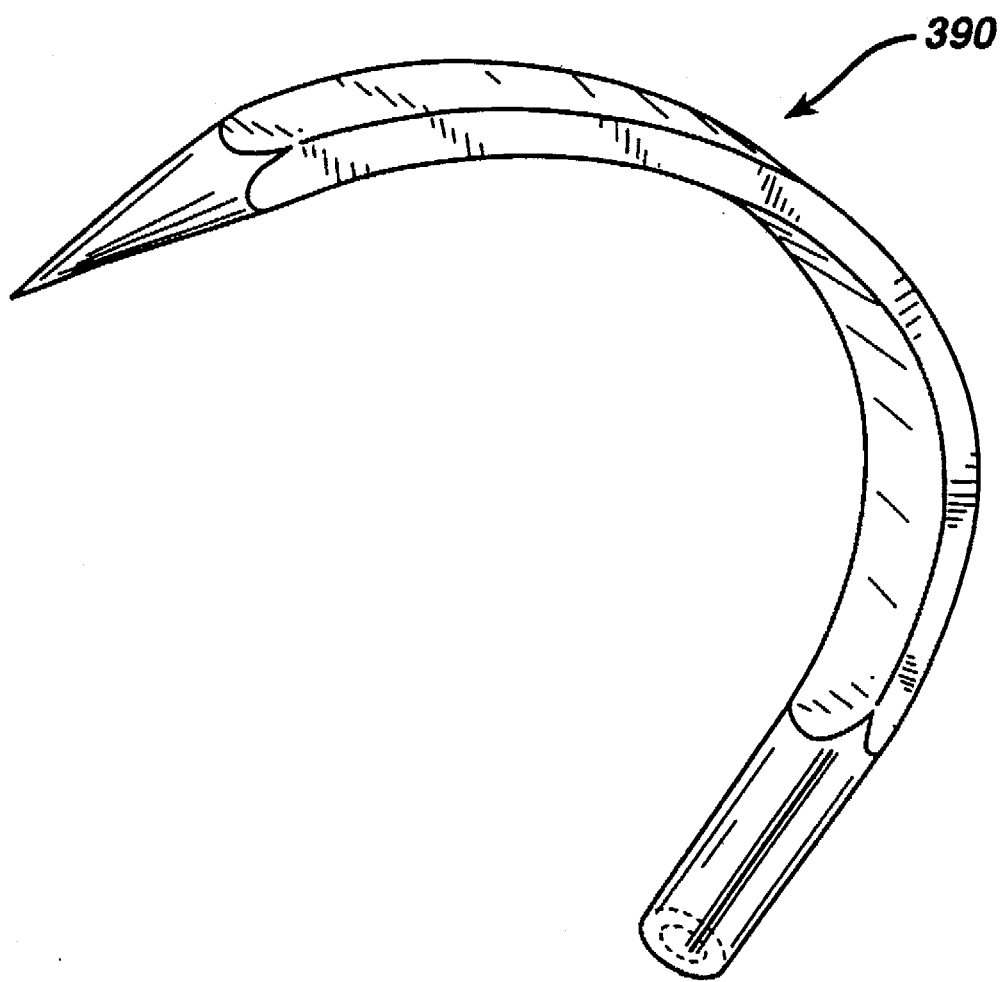
FIG. 10 is a perspective view of a needle produced by the process of FIG. 7.

An alternate process of the present invention is illustrated in FIG. 7. In that process wire 206 from roll 205 is fed by a conventional gripper/feeder machine 210 to blank cutter/carriage strip former machine 230. The roll 205 is rotatably mounted in gripper/feeder 210. Simultaneously, the carrier strip 221 is fed from carrier strip roll 220, which is rotatably mounted in conventional gripper/feeder machine 225, to blank cutter/carriage strip former machine 230. In blank cutter/carriage strip former machine 230, the wire 206 which is fed from gripper/feeder 210 is cut into lengths which are conventionally referred to as needle blanks 231. As the needle blanks 231 are being cut, the blank cutter/carrier strip former 230 is simultaneously processing the carrier strip 221. The carrier strip 221 typically consists of a steel strip known as a bandoleer. The carrier will be sufficiently thick, sufficiently wide and sufficiently flexible to effectively move and retain needle blanks while being capable of being die punched and formed. Preferably the bandoleer is made of a flexible metal such as cold rolled steel and equivalents thereof. However, the bandoleer may also be made from polymeric materials such as engineered, reinforced polymers and equivalents thereof. The wire 206 being fed from gripper/feeder 210 is cut into lengths which are conventionally referred to as needle blanks 231 within blank cutter/carriage strip former machine 230. As the needle blanks 231 are being cut, the blank cutter/carrier strip former 230 is simultaneously processing the carrier strip 221 in the following manner. Carrier strip 221 is processed to receive needle blanks 231 and to engage indexing controls within the various work stations. The carrier strip 221 is die cut, formed and crimped to produce a carrier strip having indexing pilot holes 225 and crimps which form mounting tabs 226 for receiving, engaging and holding needle blanks 231. Then, needle blanks 231 are cut and inserted into the mounting tabs 226 of carrier 221 by inserting the wire 206 into each tab 226 and then cutting the wire 206 to form a needle blank 231. The tabs 226 are then crimped to retain the needle blanks 231. The proximal ends 232 of the needle blanks 231 are bent approximately 90° from the longitudinal axis of the needle blank 231 to form tails 233. Referring to FIG. 9, a section of carrier strip 221 containing needle blanks 31 is seen. As mentioned previously in the description of the process of FIG. 1, blank cutter/strip former 230 similarly consists of several work stations.

Figure 8A:
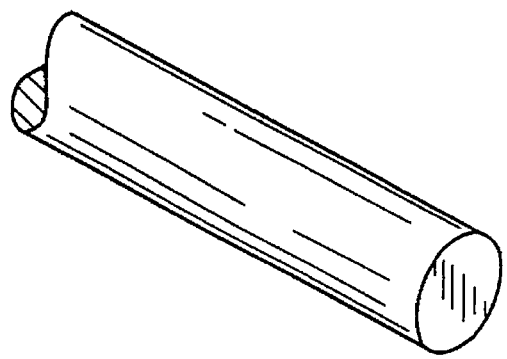
FIG. 8A–8E illustrate a progression of cross-sectional views of a needle blank after having been processed through each step of the process of FIG. 7.
Figure 8B:
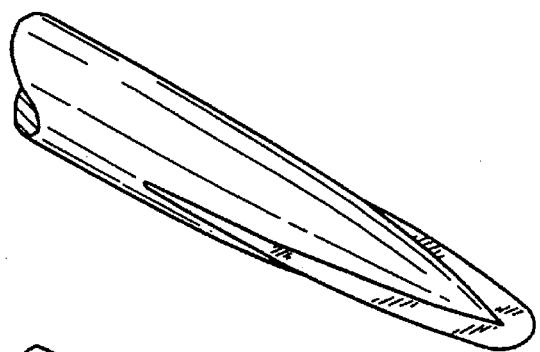
Figure 8C:
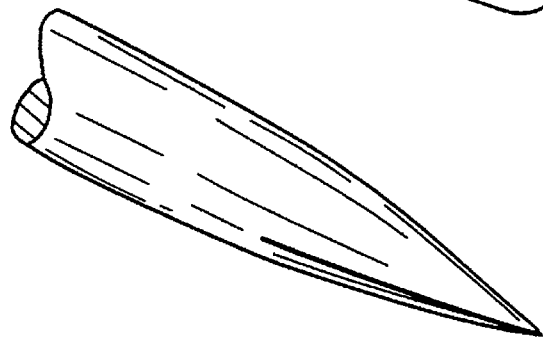
Figure 8D:
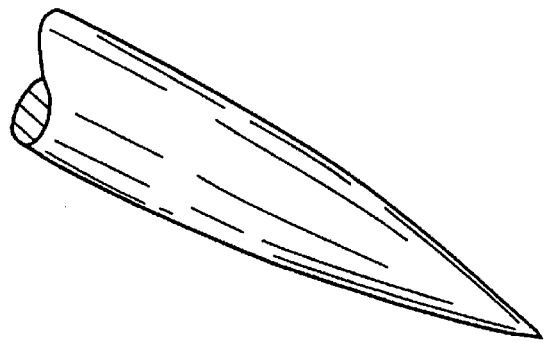
Figure 8E:
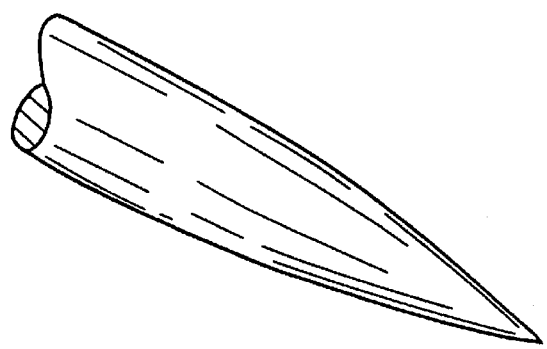
Figure 12:
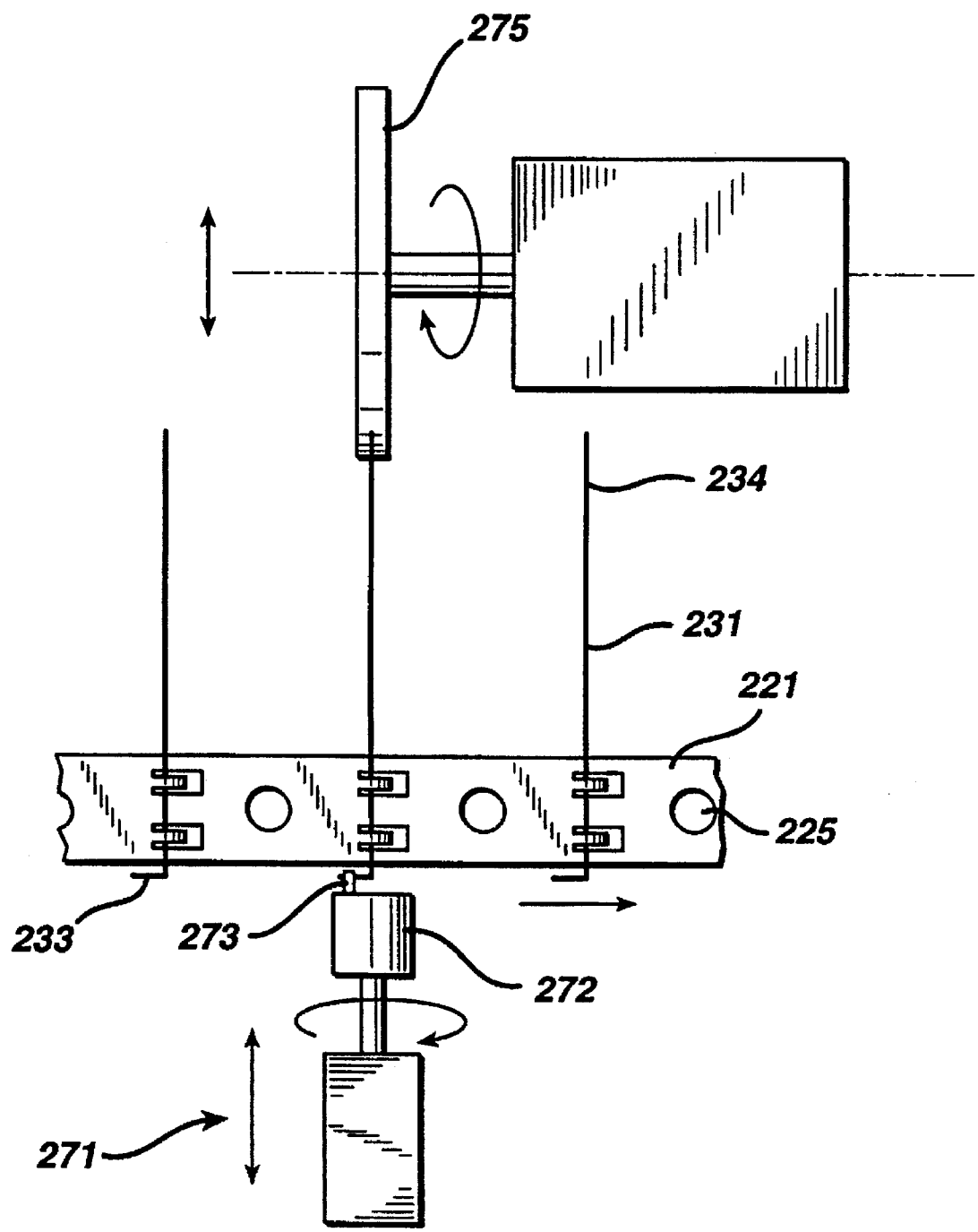
FIG. 12 is a schematic of a tail turn rotary grinding assembly; the needle blank is rotated clockwise in the carrier strip while the rotary wheel grinder grinds the needle in a direction parallel to the longitudinal axis of the needle blank.

Next, the carrier strip 221 having needle blanks 231 mounted therein is moved by a conventional gripper feeder mechanism to first coin station 240. Movement of the carrier strip to the work stations is indexed to precisely align each needle blank 231 within any of the work stations in the following manner. The carrier strip 221 has indexing pilot holes 225 punched into the carrier strip 221 by the blank cutter/strip former 230 as seen in FIG. 9. The pilot holes 225 mate with pilots mounted at each work station which engage the pilot holes 225. The pilots consist of a moveable pin which extends into the pilot holes 225. The strip 221 is indexed by a strip feed wherein pilot pins enter, engage and lock the carrier strip 221 into a precisely aligned position within a work station tool. Needle blanks 231 may be mounted at different intervals along the carrier strip 221, for example, from 0.5" to 1.0" intervals. Because of the spatial layout of the tooling, not every needle blank 231 is within a work station at a given time. Some needle blanks 231 will be indexed into a particular work station while other needle blanks 231 will be queued up waiting to enter a work station. Coining station 240 consists of a conventional closed cavity two-piece die set. The needle blank 31 is coined in station 240 by having the distal end 234 of the needle blank 231 hit with the die forcing the material into the cavities of the dies. The needle blank 31 prior to entering coining station 240 will have a configuration as seen in FIG. 8A. The needle blank 231 exiting coining station 240 has a configuration as seen in FIG. 8B. If desired, although not preferred, prior to coining station 240, the needle blank 231 may be optionally coined in an open radius die, i.e., a die without a cavity. Next the needle blank 31 is moved to trim station 250 where it is blanked with a punch and cutting die. The needle blank 31 upon exiting trimming station 250 will have a configuration as seen in FIG. 8C. If so desired, the needle blank 231 may be progressively formed in additional optional coin and trim stations such as coin station 390 and trim station 400 as seen in FIG. 7. The needle blank 231 is then moved to the top and side flattening station 260 where the needle blank 231 is given flat top and bottom sides. Then the needle blank 231 is moved to a tail turn rotary grind station 270. Tail turn rotary grind station 270 consists of a tail turning chuck 271 and a pair of grinding wheels 275. In a preferred embodiment the chuck 271 consists of pin 272 mounted to a rotating disc 273 which engages the tail 233 and rotates the needle blank 231 about its longitudinal axis within the carrier strip 221 (see FIGS. 9 and 12). The distal end 234 of needle blank 231 is simultaneously ground to a tapered point by the grinding wheels 275. Each grinding wheel 275 has one half of the profile of the desired taper point configuration. However, if desired a single grinding wheel 275 may be used or conventional grinding wheels 275 not having a contour may be used. The grinding wheel 275 or wheels 275 may have an angular or other profile. For the sake of clarity, only one grinding wheel 275 is illustrated in FIG. 12. As the needle blank 231 is turned by the chuck, the grinding wheels grind the distal end 234 of the needle blank 231 parallel to the longitudinal axis of the needle blank 231. The needle blank has a distal configuration as seen in FIG. 8D after exiting grinding station 270. The carrier strip 221 and needle blank 231 are next transported to tail turn rotary grind station 280 for processing similar or identical to that which occurs in tail turn rotary grind station 270 using similar or identical equipment, although the grit sizes of the grinding wheels may be finer. The needle blank 231 will have a distal configuration as seen in FIG. 8E after having been processed in tail turn rotary grind station 280.

The carrier strip 221 and needle blank 231 are then moved to the multiple curving anvil stations 290, 300, and 310 where the needle blank 231 is given a conventional curved configuration of a surgical needle. Next, the needle blanks 31 may be optionally turned in the tabs 26 sufficiently to effectively allow rolling the carrier 21 and needle blanks 31 onto a spool. Then, the needle blanks 231 and the carrier strip 221 are optionally washed in wash station 320. The needle blanks 231 and carrier 221 are then rolled onto a conventional spool in a conventional manner using a conventional spooling apparatus. If desired, the carrier strip may alternately be cut into strips for further processing. Next, the spool containing needle blanks 231 and the carrier strip 221 is moved to optional spool heat treat station 330 where the needle blanks 231 are heated with or without a controlled gas environment in an oven at a sufficient temperature for a sufficient amount of time to effectively make the needle blanks 231 more ductile and to improve their mechanical strength.

Next, the spool containing the carrier strips 221 and the needle blanks 231 are moved to a annealing apparatus 340 where the proximal suture mounting ends of the needles are optionally annealed. The needles are heated in a conventional annealing process at a sufficient temperature and held for a sufficient length of time at that temperature to effectively anneal the needle blanks 231. Annealing apparatus 340 consists of a conventional annealing apparatuses as previously described including a flame.

Next, the carrier strips 221 containing needle blanks 231 are moved to laser drilling station 350 where a suture mounting hole is drilled into the proximal end of each needle blank 231. The hole which is drilled by the laser is commonly referred to as a blind hole. Then, the needle blanks 231 are optionally placed into an electrochemical bath 360 and are maintained in the bath 360 for a sufficient time to effectively finish the needle blanks 231. The finished needles 370 are then removed from the electrochemical bath 360. If desired, the needles 370 may be siliconized at siliconizing station 380 by treating the needles 370 with conventional siliconizing materials in a conventional manner using conventional equipment, e.g., immersion in a tank of siliconizing material.

If desired, the process of FIG. 7 may be modified by eliminating the trim station after the initial coining station. In addition, the process may also be modified by not rotating the needle in the carrier while grinding. In such a case, the grinding would be accomplished with the grinder orbitally rotated about the needle blank. In yet another variation of the above described process, the needle is not ground and the point is formed by shearing or trimming in at least four planes to form a blank having a distal cross-section which is n-polyhedral.

The above-described processes may also be used to manufacture wire members having ends with taper points. Typically the processes would be identical wherein wire blanks would be cut from a spool of wire and progressively formed as described above. The heat treatment and curving steps could be omitted depending upon the application. In addition, one or more grinding steps could be omitted depending upon the nature and type of wire stock utilized to make the wire blanks. Such processes could be used to manufacture, for example, semiconductor leads, fasteners, pins, etc.

The terms "coined" and "coining" as used herein are defined to mean forming or reshaping a metal member by applying sufficient pressure to the member to effectively cause the metal to flow into a cavity or onto a surface of a die and to thereby assume, in whole or in part the shape of the cavity or the surface of the die.

The needle wires which can be used in the process of the present invention include conventional needle wires made from metals such as 300 series stainless steel, 400 series stainless steel, or any other wire which can be formed including conventional or known alloys.

The diameter of the needle wire used in the process of the present invention will have a diameter which will depend upon the particular alloy used. For example, the needle wire may have a diameter ranging from 0.001 inches to about 0.100 inches. More typically, wires having a diameter of about 0.010 inches to about 0.080 inches may be used, preferably about 0.015 inches to about 0.080 inches. However, other diameters may be used. The length of the needle blank 31 will vary in accordance with the type of needle which is being manufactured. The length of the needle blanks will vary in accordance with several parameters including the wire diameter, desired finished length and the type of needle.

The curving anvil machines used in the process of the present invention are conventional curving machines which operate in a conventional manner. The curving anvil machines may consist of forming elements having the desired radii. The curving anvil machines are mounted to a support frame.

The cleaning bath operates in the following manner. The carrier strip and needle blanks are placed into a reservoir containing a conventional aqueous cleaning solution such as an aqueous solution of a conventional non-caustic detergent. A conventional ultrasonic transducer is mounted in the reservoir. A conventional ultrasonic generator drives the transducer. The needle blanks and strips are rinsed and dried prior to removal from bath using a clear hot water rinse followed by a high velocity air flow.

A carrier strip cutter, if used in place of spooling, operates in the following manner. As the carrier strip is fed into the carrier strip cutter, a conventional die and punch is used to cut the strip into pre-determined lengths.

The heat treatment apparatus operates in the following manner utilizing the following cycle. Rolls of carrier containing needle blanks are placed onto trays. The trays are then loaded into a conventional heat treatment oven. The oven is brought to a sufficiently high temperature for a sufficient length of time to effectively heat treat the needle blanks. The process cycle temperatures and times are conventional in the art for processing metals.

The annealing apparatus used in the present invention consists of a conventional apparatus as previously described. The laser drilling apparatus consists of any conventional laser system having sufficient power and accuracy to effectively and repeatedly drill blind holes in needle blanks or needles.

The electrochemical bath apparatus consists of a conventional anodic electrochemical bath. Residence time of the needle blanks in the bath will be sufficient to effectively remove any residual material which may be present on the needle blank 31 to improve the surface finish. The chemical composition of the bath and voltages are conventional in this art. The electrochemical bath mixture comprises an aqueous, acidic mixture.

The electrochemical bath operates in the following manner. The needles are placed upon a metal conveyor belt which transports the needles through the aqueous bath for a sufficient amount of time at a sufficient voltage to effectively remove residual material such as residual metal flash from the needle blanks, thereby forming the finished needles.

Figure 5:
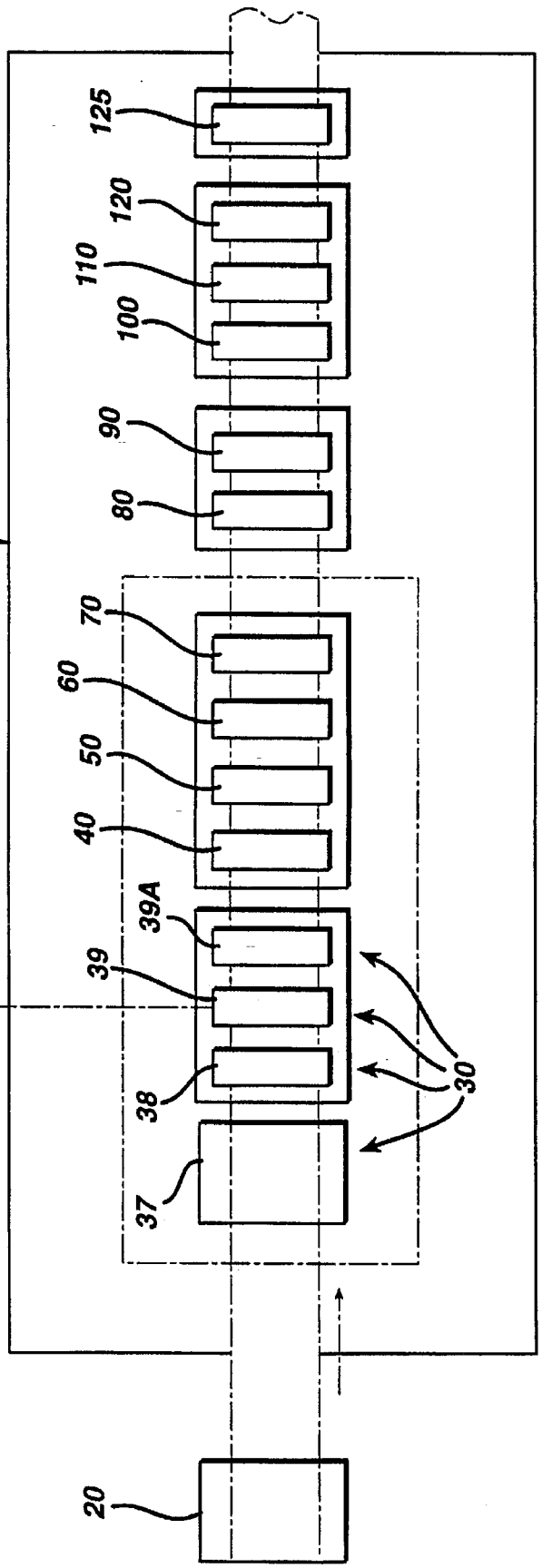
FIG. 5 is a schematic of a layout of the equipment used to manufacture a needle using the process of FIG. 1.
Figure 11:
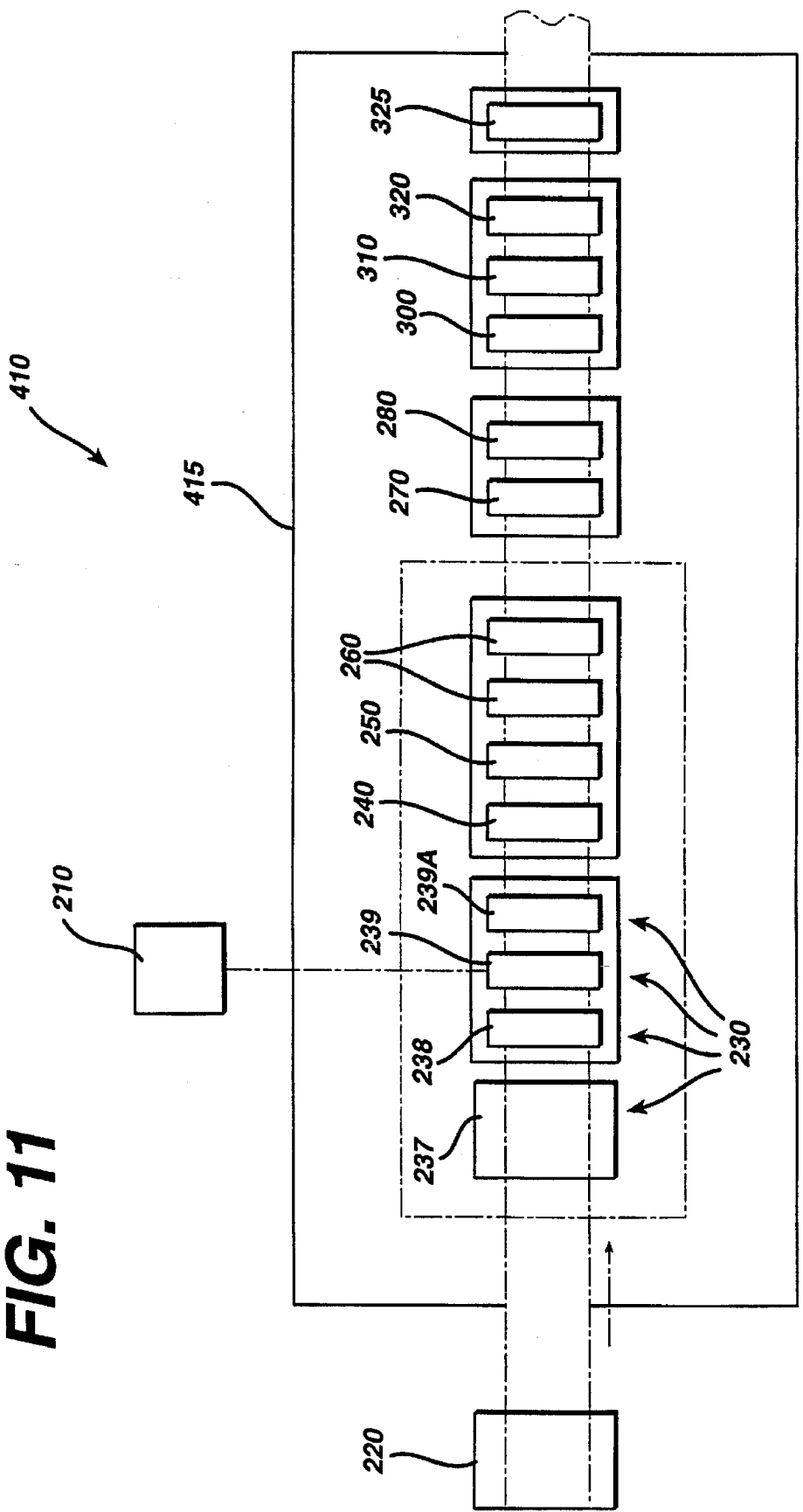
FIG. 11 is a schematic of a layout of process equipment used to manufacture a needle using the process of FIG. 7.

The coining stations, grinding stations and trimming stations utilized in the process of the present invention will consist of punches and dies mounted to frames which are in turn preferably mounted to a unitary forming machine (see FIGS. 5 and 11). It will be appreciated that in automated progressive forming processes of the type described, a needle blank will be successively be moved through the various work stations. At any given time as a needle blank 31 enters a particular station there will be other needle blanks entering a subsequent or previous stations. All of the stations are operating on different needle blanks at substantially the same point in time so that, for example, as the needle blank 31 is moved to the shear station 40 from the blank cutter/carriage strip former 30, a needle blank 31 is being moved to the curving anvil 110 from tail turn rotary grind station 90. The cleaning baths, the spool heat treatment stations, the annealing apparatuses, the laser drilling apparatuses, and the electrochemical bath 170 are typically not mounted to the forming machine.

The forming machine 195 used in the process of FIG. 1 consists of a central frame or base 196. Mounted to the base 196 are the various work stations which consist primarily of punches and dies and the grinders 85. The punches and dies are powered in a conventional manner. For example, the work stations may be powered by a motor which powers a flywheel having a clutch which in turn transmits power to the work stations with shafts, spur gears and bullgears. The flywheel is also used to create motion to drive various elements in multiple directions to facilitate the process, e.g., wheels are moved in and out along with guides, and other motions are utilized. The grinders 85 are powered by electric motors. The blank cutter/strip former station 30 is seen to consist of four individual stations including strip forming tool station 37, strip preparation tool station 38 and wire cut-off and strip crimping tool station 39 and tail bending unit 39A. A schematic of the lay-out of the forming machine 195 is seen in FIG. 6. Sufficient force is exerted upon the dies by the punches to effectively coin the wire blanks at each coining station. The forces will depend on the wire material, wire diameter, tool configuration, die configuration, etc. Typically the forces will range from up to about 30 tons or more. However, it will be appreciated that the forces may vary higher or lower depending upon the configuration of the dies and the diameter and material of the needle blank 31. The forming machine 195 will preferably have a modular configuration wherein various stations can be added, removed or interchanged as desired to vary the process.

A similar layout for the forming machine 410 used to manufacture needles in the process of FIG. 7 is seen in FIG. 11. The forming machine 410 will operate in a manner similar to that of machine 195. The forming machine 410 has frame 415. The machines are identical except that machine 410 will have coining and trimming stations instead of shear stations. Mounted to the base 415 are the various work stations which consist primarily of punches and dies and the grinders 285. The punches and dies are powered in a conventional manner. For example, the work stations may be powered by a motor which powers a flywheel having a clutch which in turn transmits power to the work stations with shafts and bullgears. The grinders 285 are powered by electric motors. The blank cutter/strip former station 230 is seen to consist of four individual stations including strip forming tool station 237, strip preparation tool station 238 and wire cut-off and strip crimping tool station 239 and tail bending machine 239A. A schematic of the lay-out of the forming machine 410 is seen in FIG. 11. The forming machine 410 will preferably have a modular configuration wherein various stations can be added, removed or interchanged as desired to vary the process.

Figure 13:
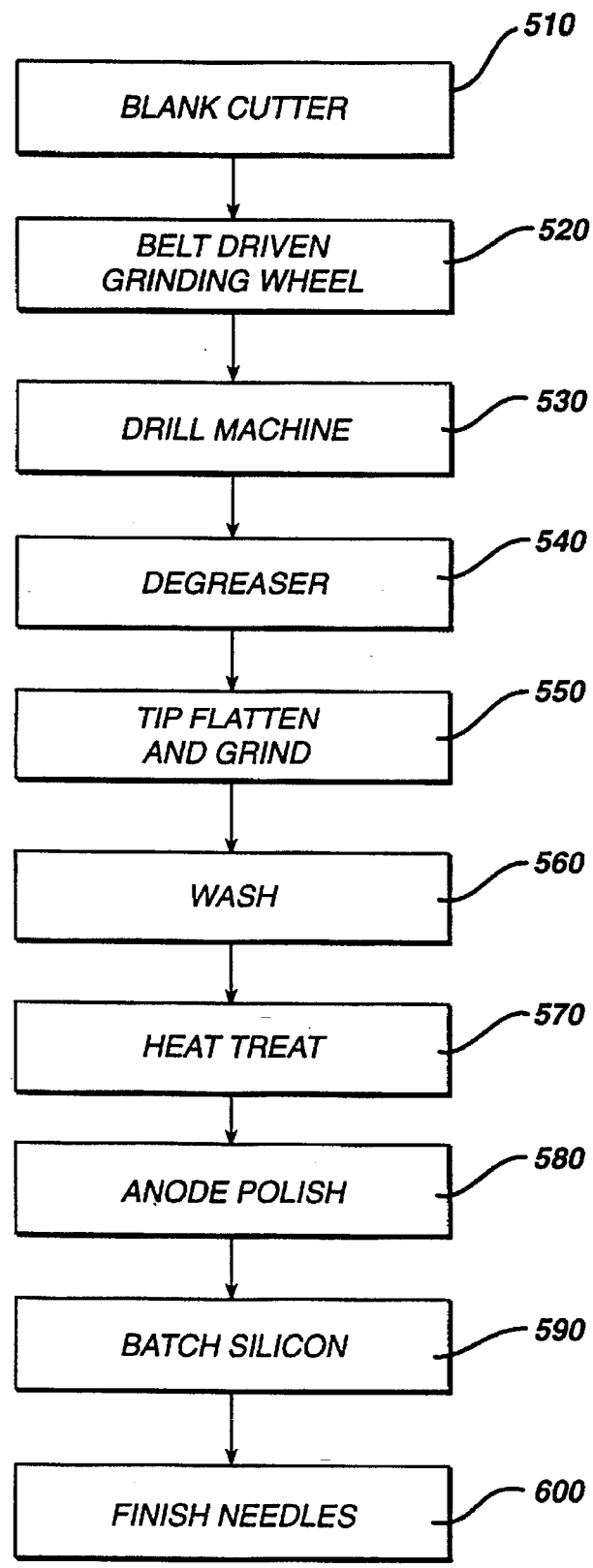
FIG. 13 is a flow diagram illustrating a prior art process for manufacturing taper point needles.
Figure 14A:
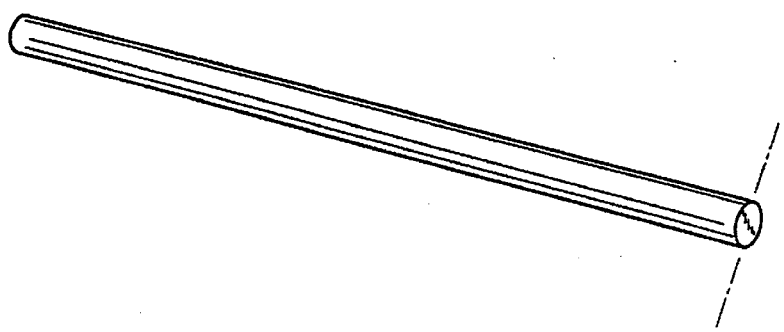
FIG. 14A–14D illustrate a progression of cross-sectional views of a needle blank after having been processed through each step of the prior art process of FIG. 12.
Figure 14B:
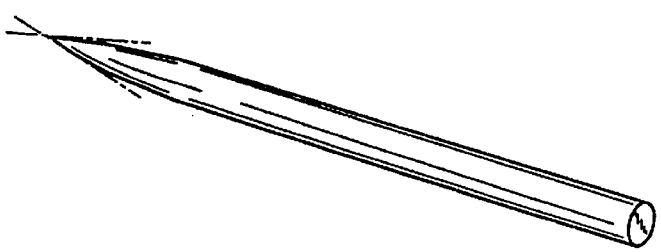
Figure 14C:
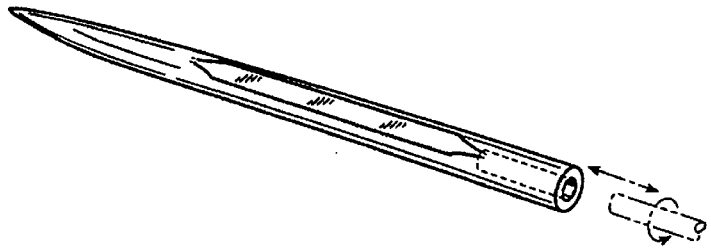
Figure 14D:
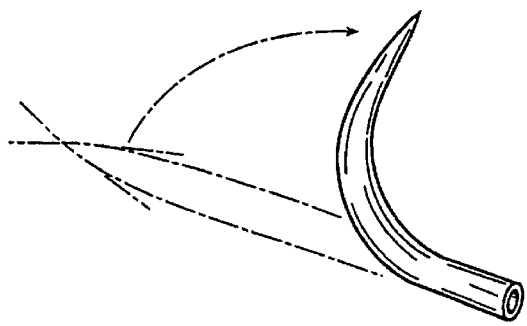
Figure 15:
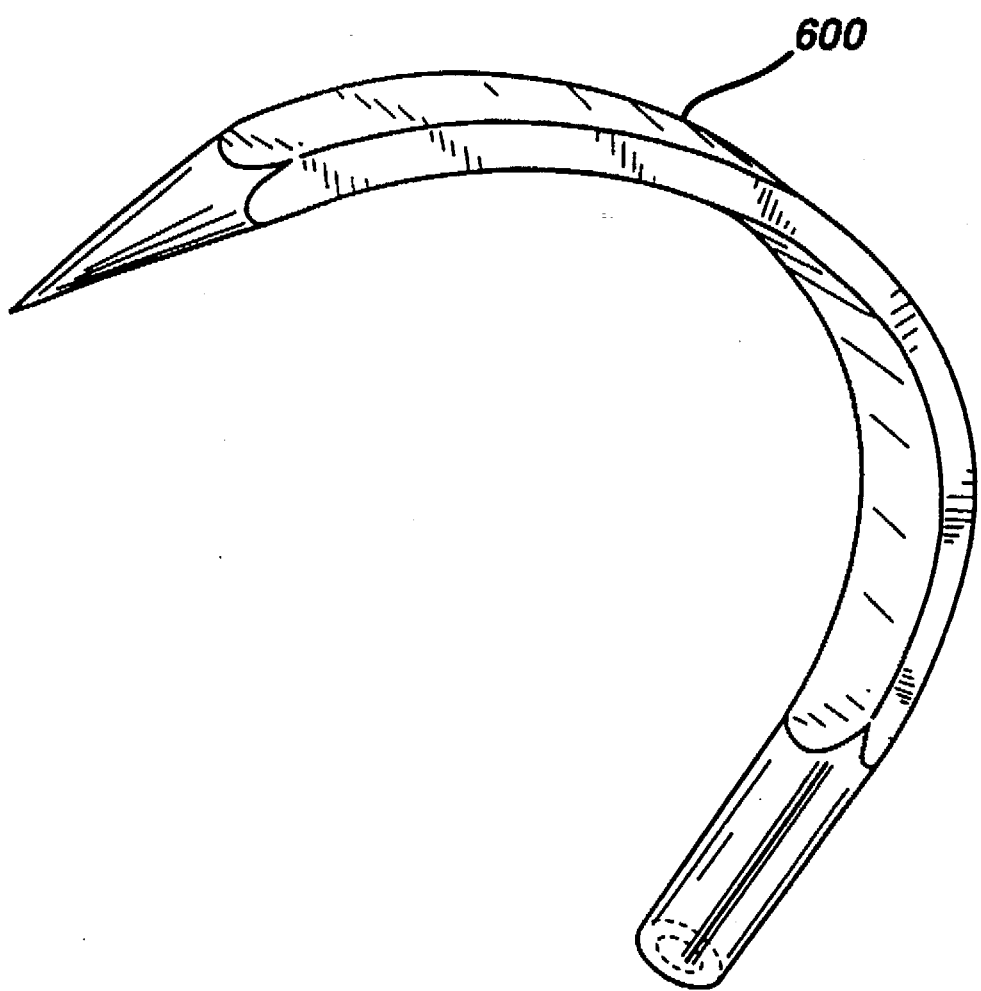
FIG. 15 is a perspective view of a needle manufactured by the prior art process of FIG. 12.

A process of the prior art for manufacturing taper point needles illustrated in FIG. 13. In that process needle blanks 500 are cut from a spool of wire in blank cutting machine station 510 and placed into a bulk container. A needle blank 500 prior to processing is illustrated in FIG. 14A. Initially, the blank 500 is given a rough distal taper point in first belt driven grinding wheel machine 520 as illustrated in FIG. 14B. The needle blanks 500 are then transferred in bulk and mounted into individual chucks in drilling machine 530. The needle blank 500 has a configuration as seen in FIG. 14C after the drilling operation in machine 530. Next the needles are degreased at station 540 in a conventional degreasing apparatus. Then the needle blanks 500 are moved in bulk to machine station 550 wherein the final curved configuration given to each needle blank 500 and the final tip is ground onto the needle blank (see FIG. 14D). The needle blanks are also give flat top and bottom sides at station 550. Then the needles are moved in bulk to conventional heat treatment station 570, anode polish station 580 and batch siliconization station 590 to produce finished needles 600. A finished needle 600 is seen in FIG. 15.

There are numerous disadvantages associated with the process of the prior art. The disadvantages include low manufacturing and process throughput speeds, inconsistency and manufacturing tolerance variation. In addition, the prior art process may subject needles to process damage, including point dulling. Another disadvantage is that the process equipment utilized in the prior art process tends to have inherent process variability due to the equipment design. Furthermore, the prior art process requires frequent material transfer in the form of loose needle blanks from machine to machine.

Although this invention has been shown and described with respect to detailed embodiments thereof, it will understood by those skilled in the art that various changes in form and detail thereof may be made without departing from the spirit and scope of the claimed invention.

We claim:

1. A method for manufacturing a taper point surgical needle comprising:

mounting a plurality of surgical needle blanks to a flat carrier strip, each surgical needle blank having a proximal angulated end; and, moving each surgical needle blank to a rotary grinding wheel and simultaneously grinding the distal end of the surgical needle blank while rotating the surgical needle blank in the carrier strip by engaging the proximal end of the surgical needle blank with a rotating means to form a taper point.

* * * * *